(12) United States Patent
Wierzba et al.

(10) Patent No.: US 12,226,146 B2
(45) Date of Patent: Feb. 18, 2025

(54) METHOD AND APPARATUS FOR FILTERING

(71) Applicant: Buffalo Filter LLC, Lancaster, NY (US)

(72) Inventors: Michael Paul Wierzba, Sloan, NY (US); Kyrylo Shvetsov, Depew, NY (US); Samantha Bonano, Williamsville, NY (US); Gregory Pepe, Lancaster, NY (US)

(73) Assignee: Buffalo Filter LLC, Lancaster, NY (US)

( * ) Notice: Subject to any disclaimer, the term of this patent is extended or adjusted under 35 U.S.C. 154(b) by 0 days.

(21) Appl. No.: 17/983,810

(22) Filed: Nov. 9, 2022

(65) Prior Publication Data
US 2023/0078525 A1    Mar. 16, 2023

Related U.S. Application Data

(63) Continuation of application No. 16/169,281, filed on Oct. 24, 2018, now Pat. No. 11,559,621.

(Continued)

(51) Int. Cl.
A61B 18/14 (2006.01)
A61B 18/12 (2006.01)
A61M 1/00 (2006.01)

(52) U.S. Cl.
CPC ...... *A61B 18/1477* (2013.01); *A61B 18/1206* (2013.01); *A61B 18/1402* (2013.01);
(Continued)

(58) Field of Classification Search
CPC ............ A61B 18/1477; A61B 18/1206; A61B 18/1402; A61B 2218/008;
(Continued)

(56) References Cited

U.S. PATENT DOCUMENTS 4,619,672 A   10/1986   Robertson
4,968,298 A   11/1990   Michelson
(Continued)

FOREIGN PATENT DOCUMENTS

CN   102240490 A1   11/2011
CN   203750318 U    8/2014
(Continued)

OTHER PUBLICATIONS

Sutherland (2008) "Basic Principles," Filters and Filtration Handbook, Elsevier Science, 5th Edn., Chapter 1: pp. 1-40.

Primary Examiner — Ankit D Tejani
Assistant Examiner — Joshua Brendon Solomon
(74) Attorney, Agent, or Firm — Timothy W. Menasco, Esq.; Harter Secrest & Emery LLP

(57) ABSTRACT

Embodiments of the present disclosure provide a method and apparatus for filtering and surgical procedures. An exemplary apparatus includes an evacuation tube having a filter, a long axis and a hollow conduit extending through the long axis, the hollow conduit fluidly connecting a tube inlet and a tube outlet, the filter located within the hollow conduit operable to remove particles from a flow passing through the hollow conduit from the tube inlet to the tube outlet.

17 Claims, 7 Drawing Sheets

Related U.S. Application Data

Figure 1:
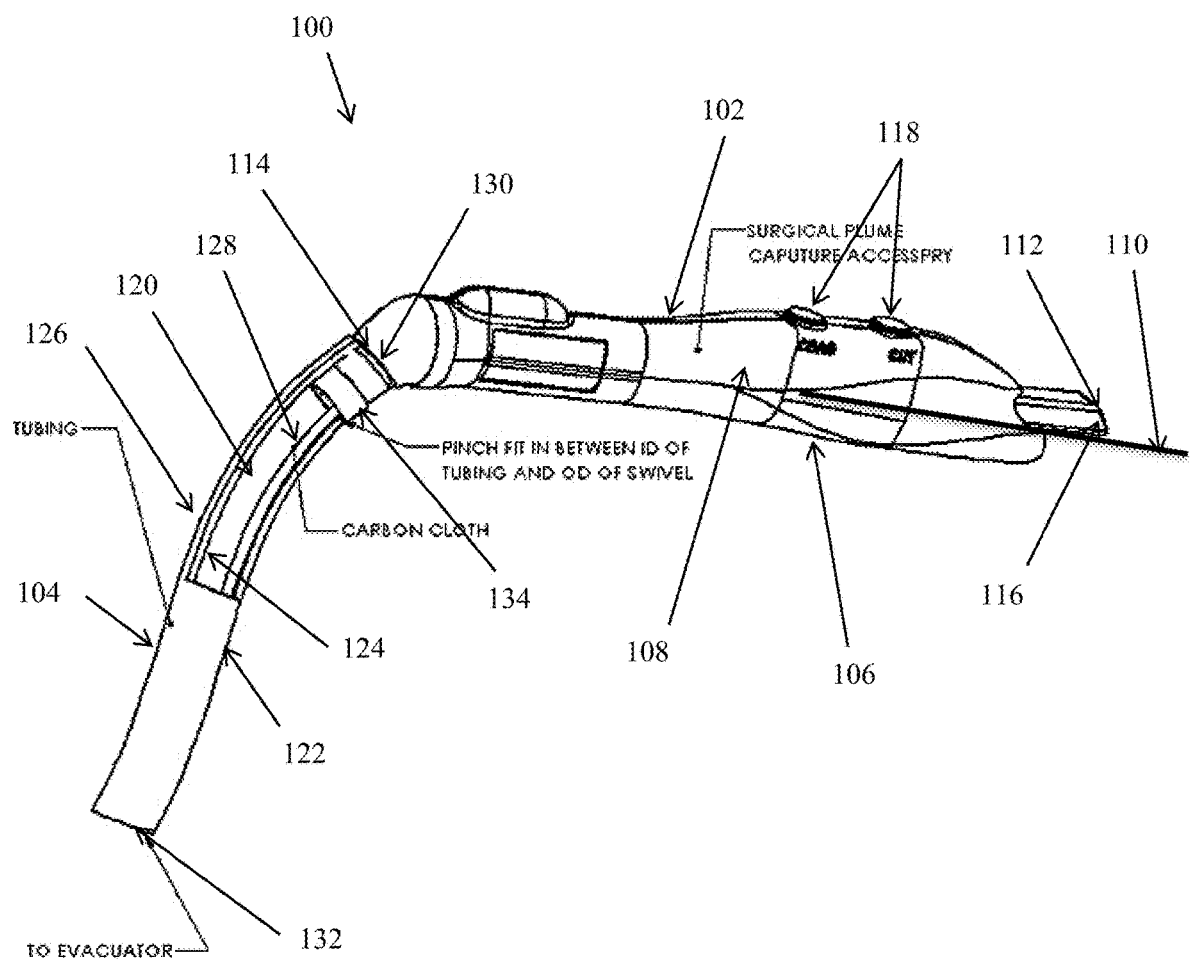

(60) Provisional application No. 62/576,301, filed on Oct. 24, 2017.

(52) U.S. Cl.
CPC .............. *A61M 1/79* (2021.05); *A61M 1/84* (2021.05); *A61B 2218/008* (2013.01); *A61M 2205/7527* (2013.01); *A61M 2205/7545* (2013.01)

(58) Field of Classification Search
CPC ........... A61B 2018/00601; A61B 2018/00922; A61M 1/79; A61M 1/84; A61M 1/784; A61M 2205/7527; A61M 2205/7545; B01D 35/30; B01D 39/2055
See application file for complete search history.

(56) References Cited

U.S. PATENT DOCUMENTS

| | | | |
|---|---|---|---|
| 5,423,779 A | 6/1995 | Yeh | |
| 5,439,587 A | 8/1995 | Stankowski et al. | |
| 5,597,385 A | 1/1997 | Moerke | |
| 5,606,966 A * | 3/1997 | Smith | B01D 39/1623 128/200.26 |
| 5,666,950 A | 9/1997 | Smith | |
| 5,709,675 A | 1/1998 | Williams | |
| 5,779,649 A | 7/1998 | Herbert | |
| 5,910,291 A | 6/1999 | Skalla et al. | |
| 5,968,032 A | 10/1999 | Sleister | |
| 6,045,596 A | 4/2000 | Holland, Jr. et al. | |
| 6,203,590 B1 | 3/2001 | Byrd et al. | |
| 6,406,454 B1 | 6/2002 | Hajianpour | |
| 6,544,210 B1 | 4/2003 | Trudel et al. | |
| 6,585,791 B1 | 7/2003 | Garito et al. | |
| 8,147,577 B2 | 4/2012 | Palmerton et al. | |
| 11,559,621 B2 * | 1/2023 | Wierzba | A61M 1/84 |
| 2006/0021613 A1 | 2/2006 | Overlander | |
| 2009/0005725 A1 | 1/2009 | Shorey et al. | |
| 2009/0293878 A1 | 12/2009 | Tatarek | |
| 2011/0072771 A1 * | 3/2011 | Palmerton | A61B 18/00 55/467 |
| 2013/0131580 A1 | 5/2013 | Blackhurst et al. | |
| 2013/0174525 A1 | 7/2013 | Palmerton et al. | |
| 2014/0277096 A1 | 9/2014 | Richter et al. | |
| 2016/0114281 A1 | 4/2016 | Bonano et al. | |
| 2016/0367734 A1 | 12/2016 | Gavlak et al. | |
| 2017/0056636 A1 | 3/2017 | Shadduck | |
| 2019/0117858 A1 | 4/2019 | Wierzba et al. | |
| 2019/0159830 A1 * | 5/2019 | Horner | A61B 18/1402 |

FOREIGN PATENT DOCUMENTS

| | | |
|---|---|---|
| CN | 204107201 U | 1/2015 |
| DE | 202013007576 U1 | 10/2013 |
| EP | 2929857 A1 | 10/2015 |
| EP | 3069737 A1 | 9/2016 |
| EP | 3078408 A1 | 10/2016 |
| GB | 1438565 A | 6/1976 |
| JP | S54-62436 A | 5/1979 |
| JP | 2001526070 A | 12/2001 |
| JP | 200679882 A | 3/2006 |
| WO | 94023657 A1 | 10/1994 |
| WO | 9931954 A2 | 7/1999 |
| WO | 2012106371 A1 | 8/2012 |

* cited by examiner

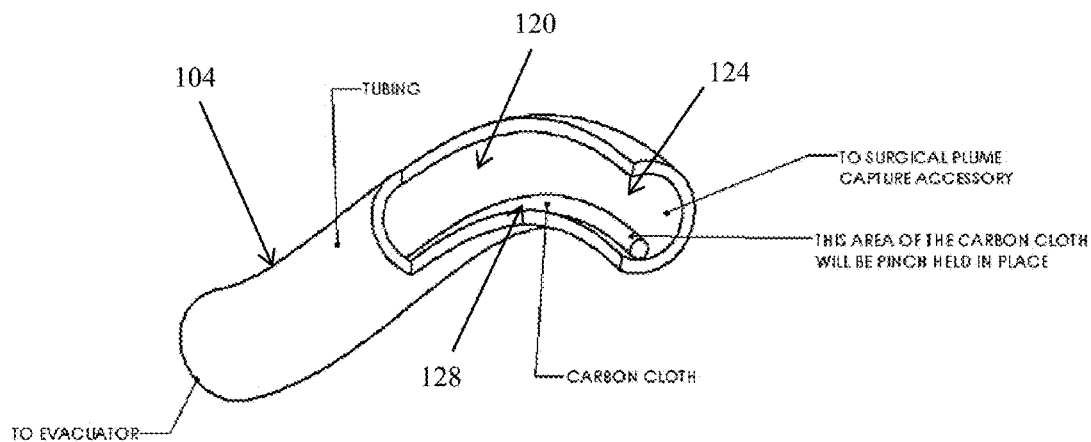
FIG. 2
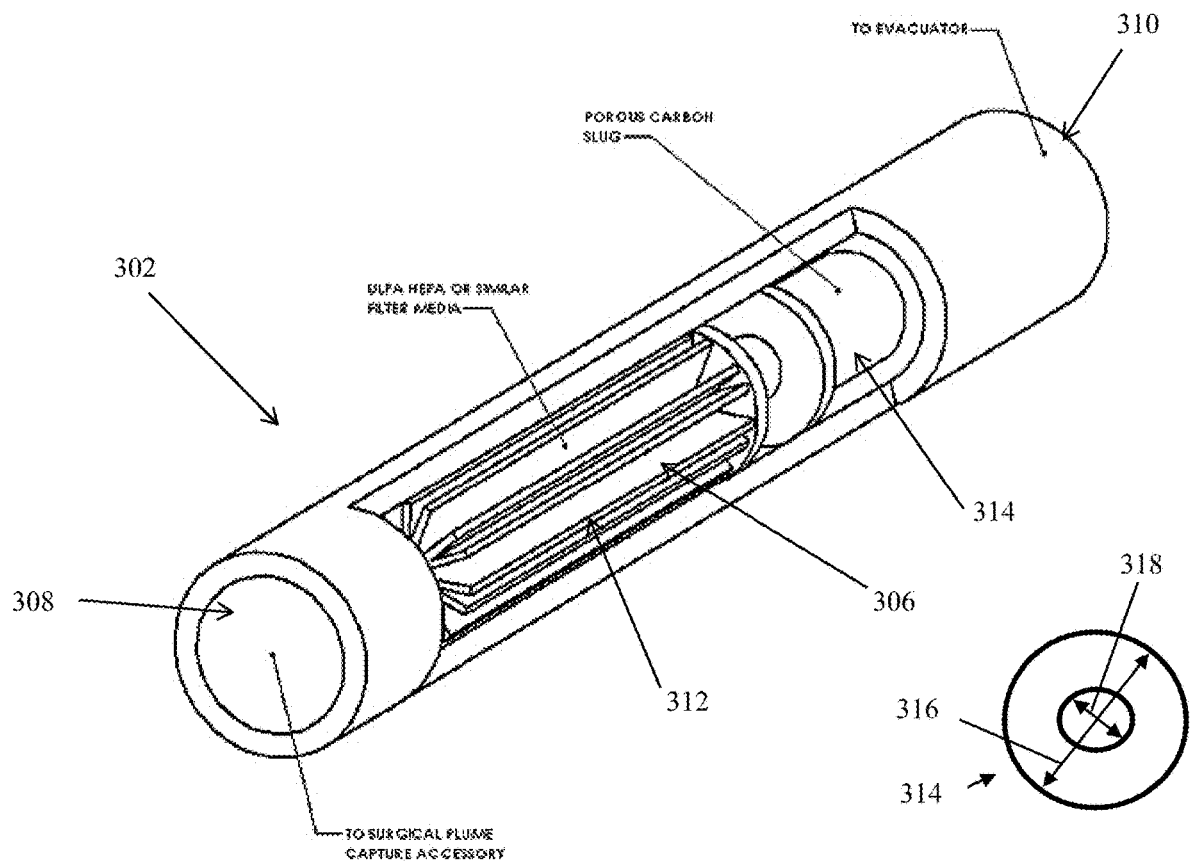
FIG. 3
FIG. 3A

800: providing a surgical device comprising a longitudinal axis and a body defining a hollow passageway extending through the longitudinal axis, the body having an inlet at a distal end of the body and an outlet at a proximal end of the body, the passageway fluidly coupled to the inlet and the outlet; and providing an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet.

802: wherein the filter comprises a carbon media extending through a portion of the long axis of the evacuation tube along an interior wall of the evacuation tube.

804: wherein the filter is a filter insert maintained within the conduit, the filter insert comprising a cylindrical body defining a hollow center, the hollow center maintaining a filter media and a carbon slug.

806: the filter comprising a plurality of filter flaps spaced apart along the long axis of the conduit, wherein each one of the plurality of filter flaps have a first portion fixedly hingedly attached to an interior wall of the conduit and a second portion removeably attached to an interior wall of the conduit, and wherein each one of the plurality of filter flaps are operable to move from first state substantially obstructing a flow through the conduit to a folded second state substantially not obstructing a flow.

808: wherein the evacuation tube comprises an unexpanded section and an expanded section, the expanded section having a diameter greater than the unexpanded section, and wherein the filter is maintained in the expanded section.

FIG. 8

METHOD AND APPARATUS FOR FILTERING

BACKGROUND OF THE INVENTION

Field of the Invention

Exemplary embodiments of the present disclosure relate to a method and apparatus for filtering. Exemplary embodiments of the present disclosure relate more particularly to a method and apparatus for filtering surgical procedures.

Description of Related Art

Surgical smoke and aerosol, or plume is created in connection with surgical procedures. For example, heat is created when a laser or electrosurgical energy is delivered to a cell. The heat causes the intracellular fluid to vaporize, which increases the pressure inside the cell and eventually causes the cell membrane to burst. A plume of smoke containing water vapor is released into the atmosphere of the operating room of the surgical procedure. Additionally, the heat can char the protein of the cell and other organic matter within the cell, and may cause thermal necrosis in cells adjacent to the surgical site. The charring of cells may also release other harmful contaminants, such as carbonized cell fragments and gaseous hydrocarbons.

BRIEF SUMMARY OF THE INVENTION

In view of the foregoing, it is an object of the present disclosure to provide an apparatus and method for filtering.

A first exemplary embodiment of the present disclosure provides an apparatus for surgical procedures. The apparatus includes a surgical device comprising a longitudinal axis and a body defining a hollow passageway extending through the longitudinal axis, the body having an inlet at a distal end of the body and an outlet at a proximal end of the body, the passageway fluidly coupled to the inlet and the outlet. The apparatus further including an evacuation tube comprising a filter, a long axis and a hollow conduit extending through the long axis, the hollow conduit fluidly connecting a tube inlet and a tube outlet, the filter located within the hollow conduit operable to remove particles from gas passing through the hollow conduit from the tube inlet to the tube outlet.

A second exemplary embodiment of the present disclosure provides an apparatus for filtering. The apparatus includes an evacuation tube comprising a filter, a long axis and a hollow conduit extending through the long axis, the conduit fluidly connecting a tube inlet and a tube outlet, the filter located within the hollow conduit operable to remove particles from a flow passing through the hollow conduit from the tube inlet to the tube outlet, wherein the filter comprises a carbon media extending through a portion of the long axis of the evacuation tube along an interior wall of the evacuation tube.

A third exemplary embodiment of the present disclosure provides an apparatus for filtering. The apparatus includes an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet, wherein the filter is a filter insert maintained within the conduit, the filter insert comprising a cylindrical body defining a hollow center, the hollow center maintaining a filter media and a carbon slug.

A fourth exemplary embodiment of the present disclosure provides an apparatus for filtering. The apparatus includes an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet, the filter comprising a plurality of filter flaps spaced apart along the long axis of the conduit, wherein each one of the plurality of filter flaps have a first portion fixedly hingedly attached to an interior wall of the conduit and a second portion removeably attached to an interior wall of the conduit, and wherein each one of the plurality of filter flaps are operable to move from first state substantially obstructing a flow through the conduit to a folded second state substantially not obstructing a flow.

A fifth exemplary embodiment of the present disclosure provides an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet, wherein the evacuation tube comprises an unexpanded section and an expanded section, the expanded section having a diameter greater than the unexpanded section, and wherein the filter is maintained in the expanded section.

A sixth exemplary embodiment of the present disclosure provides a method of filtering. The method includes providing a surgical device comprising a longitudinal axis and a body defining a hollow passageway extending through the longitudinal axis, the body having an inlet at a distal end of the body and an outlet at a proximal end of the body, the passageway fluidly coupled to the inlet and the outlet. The method further includes providing an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet.

A seventh exemplary embodiment of the present disclosure provides a method of filtering. The method includes providing an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet, wherein the filter comprises a carbon media extending through a portion of the long axis of the evacuation tube along an interior wall of the evacuation tube.

An eighth exemplary embodiment of the present disclosure provides a method of filtering. The method includes providing an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet, wherein the filter is a filter insert maintained within the conduit, the filter insert comprising a cylindrical body defining a hollow center, the hollow center maintaining a filter media and a carbon slug.

A ninth exemplary embodiment of the present disclosure provides a method of filtering. The method includes providing an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet, the filter comprising a plurality of filter flaps spaced apart along the long axis of the conduit, wherein each one of the plurality of filter flaps have a first portion fixedly hingedly attached to an interior wall of the conduit and a second portion removeably attached to an interior wall of the conduit, and wherein each one of the plurality of filter flaps are operable to move from first state substantially obstructing a flow through the conduit to a folded second state substantially not obstructing a flow.

A tenth exemplary embodiment of the present disclosure provides a method of filtering. The method includes providing an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet, wherein the evacuation tube comprises an unexpanded section and an expanded section, the expanded section having a diameter greater than the unexpanded section, and wherein the filter is maintained in the expanded section The following will describe embodiments of the present disclosure, but it should be appreciated that the present disclosure is not limited to the described embodiments and various modifications of the disclosure are possible without departing from the basic principle. The scope of the present disclosure is therefore to be determined solely by the appended claims.

BRIEF DESCRIPTION OF THE SEVERAL VIEWS OF THE DRAWING(S)

FIG. 1 presents a perspective view of an exemplary device for filtering suitable for use in practicing exemplary embodiments of this disclosure.

FIG. 2 presents a partial cross-sectional view of an exemplary tube for filtering suitable for use in practicing exemplary embodiments of this disclosure.

FIG. 3 presents another partial cross-sectional view of another exemplary tube for filtering suitable for use in practicing exemplary embodiments of this disclosure.

FIG. 3A presents a cross-sectional view of a porous slug suitable for use in practicing exemplary embodiments of this disclosure.

Figure 4:
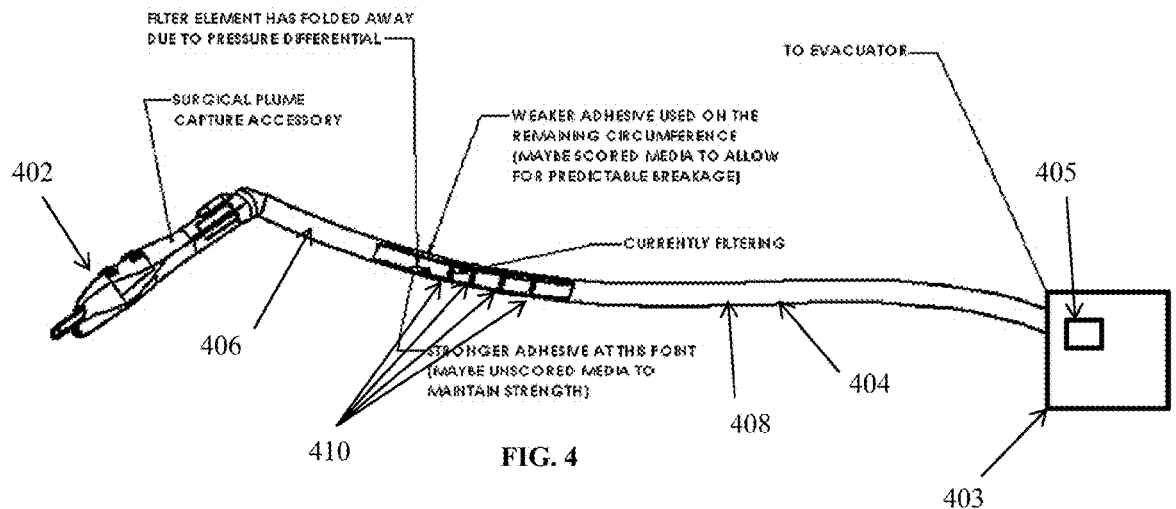

FIG. 4 presents an exemplary device and tube for filtering suitable for use in practicing exemplary embodiments of this disclosure.

Figure 5:
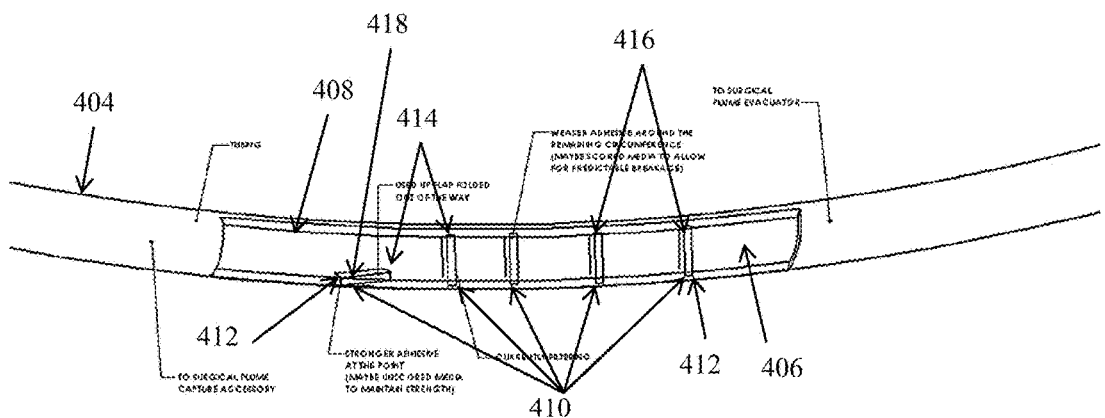

FIG. 5 presents a partial cross-sectional view of an exemplary tube for filtering suitable for use in practicing exemplary embodiments of this disclosure.

Figure 6:
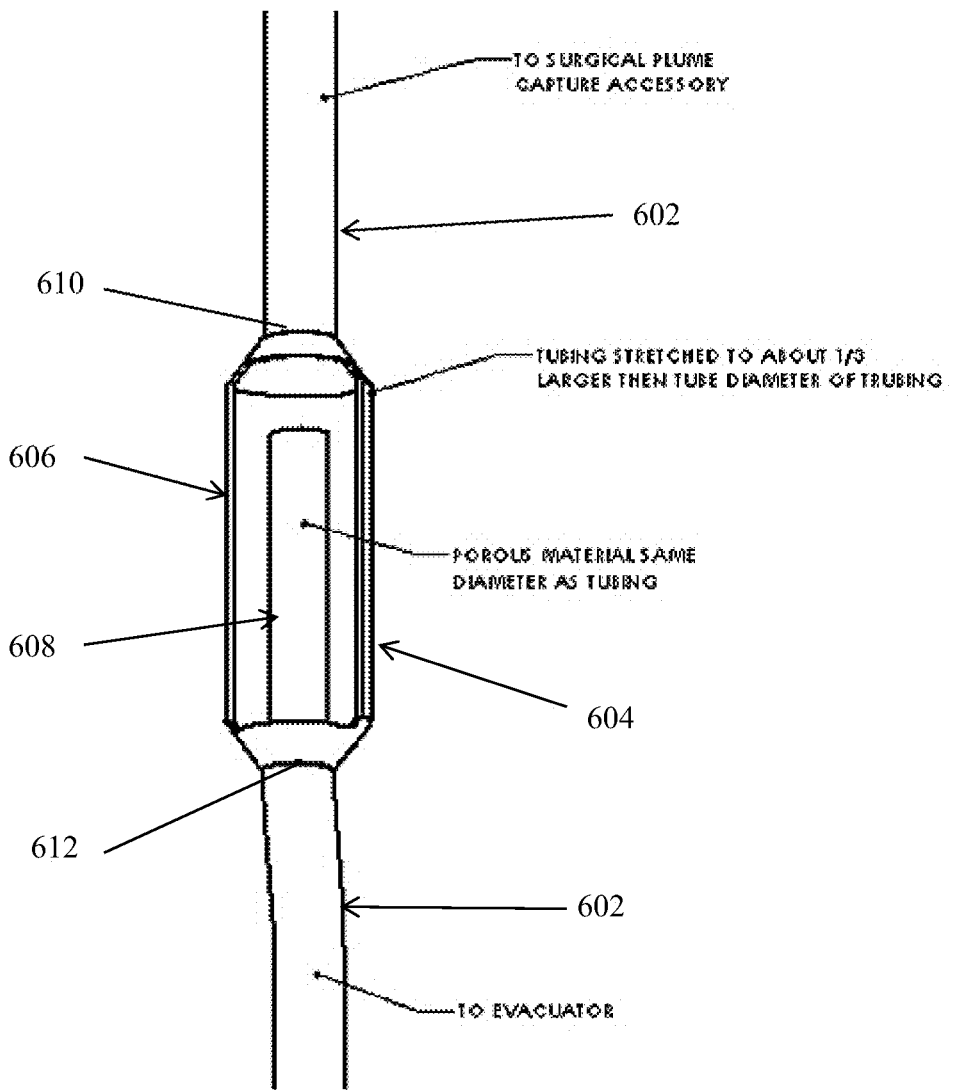

FIG. 6 presents a partial cross-sectional view of another exemplary tube for filtering suitable for use in practicing exemplary embodiments of this disclosure.

Figure 7:
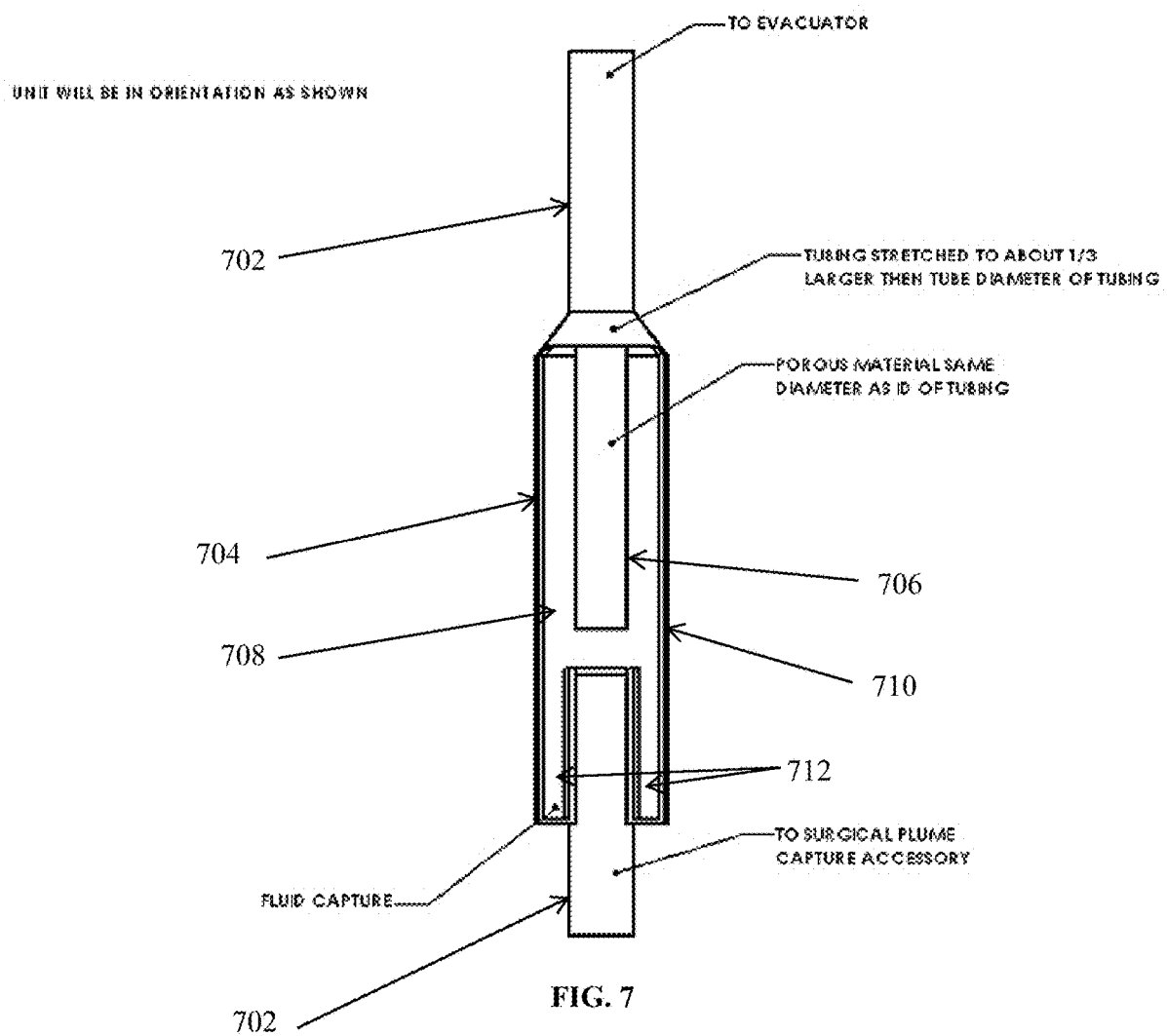

FIG. 7 presents a partial cross-sectional view of yet another exemplary tube for filtering suitable for use in practicing exemplary embodiments of this disclosure.

FIG. 8 presents a logic flow diagram in accordance with a method and apparatus for performing exemplary embodiments of this disclosure.

Figure 9:
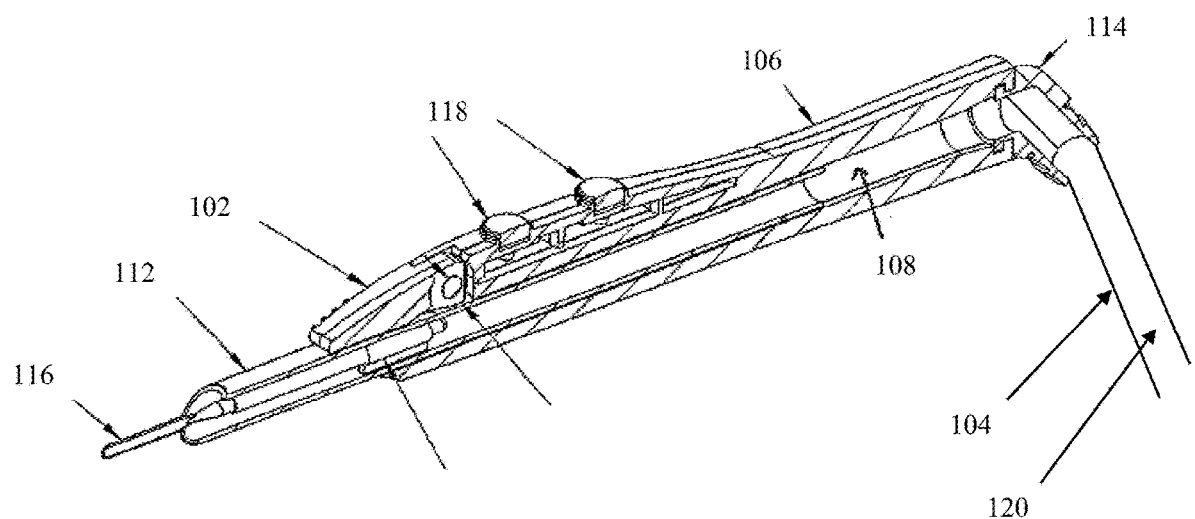

FIG. 9 presents a cross-sectional view of an exemplary device and tube for filtering suitable for use in practicing exemplary embodiments of this disclosure.

DETAILED DESCRIPTION OF THE INVENTION

Embodiments of the present disclosure provide a method and apparatus for filtering and performing surgical procedures. Embodiments present a surgical device (e.g., vacuum, vacuum tube, electrosurgical device, etc.) having a body that defines a hollow passage. The hollow passage is fluidly coupled to an evacuation tube having a hollow conduit. Embodiments provide that the hollow conduit is operable to maintain a filter operable to remove or filter particulate matter, liquid, and/or gases from air or smoke that passes through the hollow conduit. Embodiments provide that the filter can be fixedly attached within the hollow conduit of the evacuation tube such that it cannot be removed. Other embodiments provide that the filter can be removeably attached to a portion of the evacuation tube such that the filter can be replaced after use. Embodiments provide that the evacuation tube can have different diameters, it can be smooth, extruded, spiral bound and the like. Embodiments of the filter can be maintained within the evacuation tube, inside an expanded evacuation tube portion, inside a removeable filter insert accessory, and/or connected to a smoke evacuator or vacuum device. Embodiments provide that the evacuation tube is removeably attached to the surgical device.

Referring to FIG. 1, shown is an exemplary device 100 for filtering. Device 100 includes surgical device 102 and evacuation tube 104. Surgical device 102 includes a body 106, which defines or surrounds a hollow passageway 108 that extends through the longitudinal axis 110 of surgical device 102. As shown in FIG. 9, hollow passageway 108 fluidly couples inlet 112 to outlet 114. Embodiments provide that gas, smoke and/or particulate matter can pass through inlet 112, through hollow passageway 108 and through outlet 114.

Embodiments of surgical device 102 may include a surgical tool 116 (e.g., an electrode) extending from a distal end of body 106 adjacent inlet 112. Surgical device 102 may also include one or more buttons 118 for operating the surgical tool 116. Embodiments provide that surgical device 102 include electrical circuitry maintained within the body 106 for connecting the surgical tool 116 and buttons 118 to a power source for providing power to the surgical tool 116.

Also shown in FIG. 1 is evacuation tube 104 removeably coupled to the outlet 114 of surgical device 102. Evacuation tube 104 includes a long axis and a hollow conduit 120 extending through the long axis. Hollow conduit 120 is defined by an evacuation tube body 122 having an interior wall 124 and an exterior surface 126. Maintained within the hollow conduit 120 is filter 128 operable for removing smoke and particulate matter from gas or liquid that passes through conduit 120 of evacuation tube 104. Evacuation tube 104 includes a tube inlet 130 and tube outlet 132. Tube inlet 130 is fluidly removeably coupled to outlet 114. Tube inlet 130 is also fluidly coupled to hollow conduit 120 and tube outlet 132 such that particulate matter, gas and/or liquid can flow through tube inlet 130, hollow conduit 120 and tube outlet 132. Tube outlet 132 may be coupled to a vacuum or evacuation device (shown in FIG. 4) operable to pull air, gas, and/or liquid through surgical device 102, evacuation tube 102 and filter 128.

Shown in FIG. 1 is filter 128. In the embodiment shown in FIGS. 1-2, filter 128 is a carbon media extending through a portion of the long axis of evacuation tube 104 along an interior wall 124 of hollow conduit 120. For instance, filter 128 may extend through 5%, 10%, 25%, 50%, 75%, or 100% of the total length of evacuation tube 104. It should be appreciated that embodiments include filter 128 having any length greater than 0 cm and less than the total length of evacuation tube 104. Filter 128 is sized such that the cross-sectional diameter of filter 128 is less than the interior cross-sectional diameter of evacuation tube 104. In this regard, the cross-sectional diameter of filter 128 does not completely obstruct a flow of particulates, gas, and/or liquid to pass through hollow conduit 120 of evacuation tube 104.

As shown in FIG. 2, filter 128 is located along interior wall 124 of evacuation tube 104. Filter 128 is shown to have a cross-sectional circular shape. However, it should be appreciated that embodiments of filter 128 can include any cross-sectional shape including oval, rectangular, square, octagon, pentagon, star or the like. It should further be appreciated embodiments of filter 128 have a cross-sectional size that inhabits any percentage of the cross-sectional diameter of evacuation tube 104. For instance filter 128 can have a cross-section that inhabits 5%, 10%, 25%, 50%, or 75% of the cross-section of hollow conduit 120.

Embodiments of filter 128 are made of a filter media, which can include activated carbon impregnated material. Embodiments of a filter media include a cloth, woven, braided, extruded, or spun material. Embodiments of filter media can also include hydrophilic properties or it may have the ability to absorb water to prevent liquid pooling within the hollow conduit 120. The filter media can be made of material containing carbon and can have a length greater than, equal to or less than the length of the evacuation tube. For the embodiment in which the filter media is greater than the length of the evacuation tube, the filter media can be folded to extend through the length of the evacuation tube 104 multiple times. As shown in FIG. 1 and FIG. 2, filter 128 extends through hollow conduit 120 along interior wall 124 and is maintained in place through a pinch ring 134, which is operable to friction fit filter 128 between pinch ring 134 and interior wall 124. It should be appreciated that embodiments include the use of glue or a friction fit in place of pinch ring 134 to maintain a location of filter 128.

Referring to FIG. 3, shown is an exemplary filter insert 302 for use with the surgical device described herein. Embodiments of filter insert 302 are operable to take the place of filter 128 shown in FIG. 1. Shown in FIG. 3 is filter insert 302 operable to be maintained within hollow conduit 120. Filter insert 302 as shown has a cylindrical body 304 defining a hollow center 306 having an insert inlet 308 fluidly coupled to the hollow center 306 and an insert outlet 310. Hollow center 306 is operable to maintain a filter media 312 such as a ULPA, HEPA, carbon cloth or coarse particle filter. Filter media 312 can be pleated, flat, sheet shaped, or be a solid material. The filter media 312 can be pressed into place within filter insert 302, or it can be glued or mechanically bonded to the cylindrical body 304. Filter media 312 can include carbon that is impregnated material, or it can be a flat sheet of solid fused carbon. The filter insert 302 itself can be fixedly attached to or within evacuation tube 104, or it can be moveably maintained within conduit 120 such that it can be removed from evacuation tube 104. As shown in FIG. 3 filter media 312 can have a cross-section that is star shaped, however, embodiments of filter media 312 can include any shape that maximizes or increases surface area. Also maintained within filter insert 302 is a porous carbon slug 314.

Referring to FIG. 3A, shown Embodiments of porous carbon slug 314 can have a hollow cylindrically shape to maximize surface area. Embodiments of porous carbon slug 314 include a cylindrical body having a first radial section 316 having a diameter equal to an interior diameter of the filter insert 302 and a second hollow radial section 318 having a second diameter less than the interior diameter of the filter insert 302 and less than the diameter of first radial section 316. Embodiments of filter insert 302 provide a filter media 312 and a carbon slug 314 that is operable to filter out or remove particulate, gas, and/or liquid from a flow that passes through evacuation tube 104, insert inlet 308, and insert outlet 310.

Referring now to FIG. 4 and FIG. 5, shown are alternative filters operable for use with exemplary surgical devices 102 and/or evacuation tubes 104. Shown in FIG. 4 is surgical device 402 fluidly coupled to evacuation tube 404. Evacuation tube 404 includes a hollow conduit 406 defined by an interior wall 408. Evacuation tube 404 can be removeably or fixedly coupled to an evacuator or vacuum 403 operable to pull air, gas, and/or liquid through surgical device 406, evacuation tube 404 and filters. Embodiments of evacuator or vacuum 403 include at least one motor 405 for pulling air, gas, and/or liquid. Evacuation tube 404 includes a filter having a plurality of filter flaps 410 spaced apart along the long axis of the evacuation tube 404 within hollow conduit 406. Each one of the plurality of filter flaps 410 having a first portion 412 fixedly hingedly attached to interior wall 408 and a second portion 414 removeably attached to interior wall 408. Each one of the plurality of filter flaps 410 are operable to move from a first state (indicated by reference character 416) substantially obstructing a flow through the hollow conduit 406 to a second state (indicated by reference character 418) substantially not obstructing a flow through the conduit. In other words, embodiments of filter flaps 410 are operable to filter particulates, gas and/or liquid that flows through hollow conduit 406. Filter flaps 410 are sized in one embodiment such that they encompass the entire cross-section of hollow conduit 406. In other words, a flow through hollow conduit 406 upon reaching each filter flap 410 is required to pass through filter flap 410. Embodiments include there being little to no space between interior wall 408 and each filter flap 410. In this regard, in one embodiment, each filter flap 410 is sized and shaped to match the shape and size of the interior cross-section of hollow conduit 406. In another embodiment, filter flap 410 is not sized or shaped to encompass the entire cross-section of hollow conduit 406, but covers only a portion of the cross-section of hollow conduit 406. For instance, filter flap 410 may encompass 5%, 10%, 25%, 50%, 75%, or 99% of the area cross-section of hollow conduit 406. Embodiments of filter flap 410 include each filter flap 410 covering any percentage of the cross-sectional area of hollow conduit 406.

As a particular filter flap 410 gathers of filters out more and more particulate matter from passing gas and liquid, the ability for gas and liquid to pass through that particular filter flap 410 becomes more difficult. As it becomes more difficult for gas and liquid to pass through a particular filter flap 410, a pressure differential is created between opposing sides of filter flap 410. The opposing sides being the side of filter flap 410 receiving a flow and the side of filter flap 410 transmitting the flow or having the flow exit. Embodiments of filter flaps 410 provide that each filter flap 410 is operable to fold or hingedly move from the first state 416 to the second state 418 in response to a pressure differential between opposing sides of the filter flap 410 exceeding or meeting a predetermined threshold. The predetermined threshold is met when a particular filter flap 410 allows little to no flow through filter flap 410. In other words, as a particular filter flap 410 continues to filter out particulate from the flow that passes through it, the continued ability for the flow to pass through that particular filter flap 410 decreases. The accumulated particulate or liquid for a particular filter flap 410 prevents or obstructs the flow of gas to pass through filter flap 410. When a particular filter flap 410 is unable to allow a flow through it, pressure builds and becomes greater on the side of filter flap 410 that receives the flow than on the side of the filter flap 410 that transmits the flow. This pressure differential causes a particular filter flap 410 to fold at the first portion 412 thereby alleviating the pressure differential.

Each filter flap 410 is operable such that the filter flaps 410 will move from a first state 416 to a second state 418 in the order that filter flaps 410 receive the flow. In other words, the first filter flap 410 to receive the flow will be the first to move from a first state 416 to a second state 418. Then the second filter flap 410 to receive the flow will be the second to move from a first state 416 to a second state 418. This will continue until all of the filter flaps 410 are in the second state 418 at which point the evacuation tube 404 will need to be replaced having new filter flaps 410. It should be appreciated that embodiments provide that multiple filter flaps 410 may simultaneously move from a first state 416 to a second state 418.

Embodiments of filter flaps 410 include that each filter flap 410 be fixedly attached to the interior wall of hollow conduit 406 such that filter flaps 410 do not move or fold. Embodiments of filter flaps 410 can be maintained directly within evacuation tube 404 or can be an element of a filter insert as a filter media shown in FIG. 3. Embodiments of filter flaps 410 are made of ULPA, provide HEPA level filtration, are fused polystyrene spheres, activated carbon, or other filtration media.

Reference is now made to FIG. 6, which depicts another exemplary filter for use with an evacuation tube. Shown in FIG. 6 is evacuation tube 602 and filter capsule 604. Embodiments of filter capsule 604 include filter capsule 604 being integral with evacuation tube 602 wherein evacuation tube 602 may be an unexpanded section and filter capsule 604 is an expanded section having a diameter greater than the unexpanded section. Embodiments also provide that filter capsule 604 is a separate element from evacuation tube 602 that is fixedly attached between two ends (610, 612) of evacuation tube 602. Filter capsule 604 has a hollow body 606 that maintains a filter 608. Filter 608 can be made of a porous material such as ceramic polymer or metal. Filter 608 can also include a pleated or flat sheet media or it can be solid or porous material. Embodiments of filter 608 are cylindrically shaped or can be any shape operable to be maintained within hollow body 606 to maximize surface area (e.g., square, oval, rectangular, octagon, pentagon, etc.). Filter 608 can be fixedly attached to filter capsule 604 through an adhesive or friction fit. Embodiments of filter 608 can be flexible, ridged, or semi-ridged. Embodiments of filter 608 are operable to allow bi-directional flow through filter capsule 604. Filter capsule 604 can be affixed at any point within evacuation tube 602 or within a smoke evacuator or vacuum source.

Referring to FIG. 7, illustrated is yet another exemplary filter for use with an evacuation tube. Shown in FIG. 7 is evacuation tube 702 and filter assembly 704. Filter assembly 704 includes a porous filter 706 maintained within a hollow cavity 708 defined by filter assembly body 710. Filter 706 is fixedly or removeably attached to filter assembly body 710 and can have a cylindrically shaped body with a diameter equal to or less than the diameter of evacuation tube 702. Filter assembly 704 also includes a fluid or liquid capture section 712 and a bottom portion of filter assembly 704. Embodiments of filter assembly 704 are operable to filter or remove smoke and particulate matter by filter 706 and to collect liquid within fluid capture section 712. In practice, as a flow of particulate, gas, and/or liquid passes through filter assembly 704, filter 706 filters out smoke and particulate matter from the flow, and liquid falls into liquid capture section 712 thereby trapping liquid within filter assembly 704. Embodiments of filters shown in FIG. 6 and FIG. 7 provide that filter capsule 604 and filter assembly 706 be oriented vertically as shown.

In practice, embodiments of the present disclosure provide that a surgical device such as an electrosurgical device can be used to cut tissue during a surgical procedure. The cutting can cause surgical smoke to be created. Embodiments provide a surgical device coupled to an evacuation tube and an evacuator or vacuum can pull the surgical smoke through a passageway within the surgical device, through the evacuation tube and through a filter maintained within or attached to the evacuation tube. Thus, surgical smoke and other particulate matter is filtered out of the air as it passes through the filter in the evacuation tube. Embodiments provide that the evacuation tube be integral with the filter such that replacement of the filter would require replacement of the evacuation tube. In other embodiments, the filter is removeably affixed to the evacuation tube such that replacement of the filter only requires replacement of the filter and not the evacuation tube.

Reference is now made to FIG. 8, which depicts a logic flow diagram in accordance with a method and apparatus for performing exemplary embodiments of this disclosure. Block 800 presents providing a surgical device comprising a longitudinal axis and a body defining a hollow passageway extending through the longitudinal axis, the body having an inlet at a distal end of the body and an outlet at a proximal end of the body, the passageway fluidly coupled to the inlet and the outlet; and providing an evacuation tube comprising a filter, a long axis and a hollow conduit extending through the long axis, the conduit fluidly connecting a tube inlet and a tube outlet, the filter located within the hollow conduit operable to remove particles from gas passing through the hollow conduit from the tube inlet to the tube outlet. Then block 802 specifies wherein the filter comprises a carbon media extending through a portion of the long axis of the evacuation tube along an interior wall of the evacuation tube.

Some of the non-limiting implementations detailed above are also summarized at FIG. 8 following block 802. Block 804 relates to wherein the filter is a filter insert maintained within the conduit, the filter insert comprising a cylindrical body defining a hollow center, the hollow center maintaining a filter media and a carbon slug. Block 806 then states the filter comprising a plurality of filter flaps spaced apart along the long axis of the conduit, wherein each one of the plurality of filter flaps have a first portion fixedly hingedly attached to an interior wall of the conduit and a second portion removeably attached to an interior wall of the conduit, and wherein each one of the plurality of filter flaps are operable to move from first state substantially obstructing a flow through the conduit to a folded second state substantially not obstructing a flow. Block 808 specifies wherein the evacuation tube comprises an unexpanded section and an expanded section, the expanded section having a diameter greater than the unexpanded section, and wherein the filter is maintained in the expanded section.

The logic diagram of FIG. 8 may be considered to illustrate the operation of a method. The logic diagram of FIG. 8 may also be considered a specific manner in which components of a device are configured to cause that device to operate, whether such a device is a surgical device, an electrosurgical device, an evacuation tube, an evacuation or one or more components thereof.

This disclosure has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for surgical procedures, the apparatus comprising:
   an evacuation tube comprising a filter, a long axis and a hollow conduit extending through the long axis, the hollow conduit fluidly connecting a tube inlet and a tube outlet, the filter located within the hollow conduit operable to remove particles from a flow passing through the hollow conduit from the tube inlet to the tube outlet, wherein the filter comprises a carbon media extending through the long axis of the evacuation tube along an interior wall of the evacuation tube.

2. The apparatus according to claim 1, wherein the carbon media extends through a portion of the long axis of the evacuation tube along an interior wall of the evacuation tube.

3. The apparatus according to claim 2, wherein the carbon media comprises at least one of activated carbon impregnated material and activated carbon absorber.

4. The apparatus according to claim 2, wherein the filter is coupled to the interior wall of the evacuation tube with one of a pinch ring, glue, or friction fit.

5. The apparatus according to claim 1, further comprising a filter media, wherein the filter media is at least one of ULPA, HEPA and coarse particle filter.

6. The apparatus according to claim 1, further comprising a filter media, wherein the filter media is at least one of pleated, flat sheet shaped, and solid material.

7. The apparatus according to claim 1, further comprising a filter insert, wherein the filter insert is one fixedly maintained within the conduit and moveably maintained within the conduit.

8. The apparatus according to claim 1, the evacuation tube comprising a plurality of filters within the evacuation tube spaced along the long axis.

9. An apparatus for filtering, the apparatus comprising:
   an evacuation tube comprising a filter, a long axis and a hollow conduit extending through the long axis, the hollow conduit fluidly connecting a tube inlet and a tube outlet, the filter located within the hollow conduit operable to remove particles from a flow passing through the hollow conduit from the tube inlet to the tube outlet, the filter comprising a plurality of filter flaps spaced apart along the long axis of the conduit within the hollow conduit, wherein each one of the plurality of filter flaps have a first portion fixedly hingedly attached to an interior wall of the conduit and a second portion removeably attached to the interior wall of the conduit, and wherein each one of the plurality of filter flaps are operable to move from first state located within the hollow conduit substantially obstructing a flow through the conduit to a folded second state located within the hollow conduit substantially not obstructing a flow, wherein each one of the plurality of filter flaps is operable to filter particulate matter from a gas or liquid that passes through the hollow conduit and plurality of filter flaps.

10. The apparatus according to claim 9, wherein moving from the first state to the second state causes the second portion to detach from the interior wall of the evacuation tube and the first portion hingedly fold, wherein each of the first portion and the second portion are located within the hollow conduit.

11. The apparatus according to claim 9, wherein each one the plurality of filter flaps is operable to move from the first state to the second state in response to a difference in pressure on between a first side located within the hollow conduit and a second side of the filter flap located within the hollow conduit.

12. The apparatus according to claim 9, wherein each one of the plurality of filter flaps are made of at least one of ULPA and activated carbon.

13. The apparatus according to claim 9, wherein the filter is a filter insert maintained within the conduit.

14. An apparatus for filtering, the apparatus comprising:
   an evacuation tube comprising a filter, a long axis and a hollow conduit extending through the long axis, the hollow conduit fluidly connecting a tube inlet and a tube outlet, the filter located within the hollow conduit operable to remove particles from a flow passing through the hollow conduit from the tube inlet to the tube outlet, wherein the evacuation tube comprises an unexpanded section and an expanded section, the expanded section having a diameter greater than the unexpanded section, and wherein the filter is maintained in the expanded section, wherein the filter is a filter insert maintained within the hollow conduit, the filter insert comprising a cylindrical body defining a hollow center, the hollow center maintaining a filter media and a carbon slug, wherein the carbon slug comprises a cylindrical body defining a hollow center, and wherein the cylindrical body comprises a first radial section having a diameter equal to an interior diameter of the evacuation tube and a second radial section having a second diameter less than the interior diameter of the evacuation tube.

15. The apparatus according to claim 14, wherein the filter comprises at least one of ceramic, polymer, porous material, metal, planar sheet media and a solid porous material.

16. The apparatus according to claim 14, wherein the filter is fixedly maintained within the expanded section by one of adhesive and friction fit.

17. The apparatus according to claim 14, wherein the filter is operable to remove particulate matter and liquid from fluid that passes through the conduit, and wherein the filter comprises a fluid capture section.

* * * * *